United States Patent [19]

Ribalta-Baro et al.

[11] Patent Number: 5,132,304
[45] Date of Patent: Jul. 21, 1992

[54] BENZOTHIAZINE DERIVATIVES AND THEIR APPLICATIONS AS MEDICINAL PRODUCTS OR AS SYNTHESIS INTERMEDIATES FOR MEDICINAL PRODUCTS

[75] Inventors: José M. Ribalta-Baro, Esplugues de Llobregat; Jordi F. Rigola-Constansa, Barcelona, both of Spain

[73] Assignee: Laboratorios Del Dr. Esteve, S. A., Barcelona, Spain

[21] Appl. No.: 560,125

[22] Filed: Jul. 31, 1990

[30] Foreign Application Priority Data

Aug. 4, 1989 [FR] France ............... 89 10537

[51] Int. Cl.$^5$ ............... A61K 31/54; C07D 417/12
[52] U.S. Cl. ............... 514/226.5; 544/49
[58] Field of Search ............... 514/226.5; 544/49

[56] References Cited
U.S. PATENT DOCUMENTS
4,623,486  11/1986  Lombardino ............... 514/226.5

Primary Examiner—Patricia L. Morris
Attorney, Agent, or Firm—Dressler, Goldsmith, Shore, Sutker & Milnamow, Ltd.

[57] ABSTRACT

The invention relates to the compounds corresponding to the general formula I

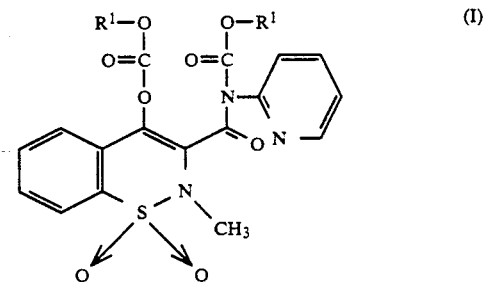

in which:

$R^1$ represents a lower alkyl radical (having one to four carbon atoms), a phenyl radical or a benzyl radical. These compounds are useful as medicinal products or as synthesis intermediates for medicinal products.

4 Claims, No Drawings

BENZOTHIAZINE DERIVATIVES AND THEIR APPLICATIONS AS MEDICINAL PRODUCTS OR AS SYNTHESIS INTERMEDIATES FOR MEDICINAL PRODUCTS

The present invention relates to new chemical compounds corresponding to the general formula I, to a process for preparing these and also to their applications as medicinal products or for the preparation of medicinal products:

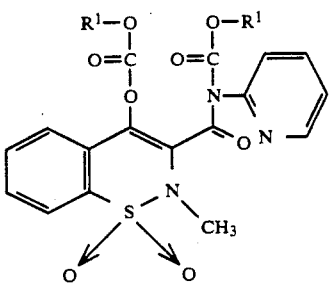

in which $R^1$ represents a $C_1$ to $C_4$ lower alkyl radical, a phenyl radical or a benzyl radical.

Oxazinobenzothiazine 6,6-dioxides of general formula II, in which $R^2$ represents a heteroaryl radical, are well known anti-inflammatory and analgesic agents, especially droxicam ($R^2$=2-pyridyl), which are described in Chem. Abst., 1984, 100, 191893j

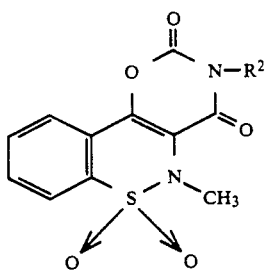

An effort has been made to obtain simple and efficacious intermediates which make it possible to provide for the synthesis of droxicam under good conditions and especially under conditions which are easy to implement on an industrial scale.

In the prior art, droxicam was prepared from an ester of formula (III)

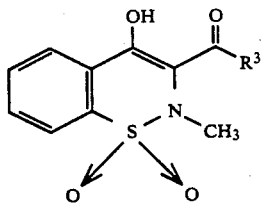

in which $R^3$ represents an alkoxy radical. Furthermore, Patents FR-A-2 566 4508 and FR-A-2,597,103 describe the preparation of droxicam from a compound of formula (III) in which $R^3$ represents a 2-pyridylamino radical.

The present invention relates to new chemical compounds corresponding to the general formula I, in which $R^1$ represents a lower alkyl radical (having 1 to 4 carbon atoms), a phenyl radical or a benzyl radical.

According to the invention, the compounds of formula I are prepared by the reaction of a compound of formula III, in which $R^3$ represents a 2-pyridylamino radical, with a compound of general formula IV

in which $R^1$ has the meaning given above in relation to the general formula I, in the presence of a base.

The reaction between the compounds of general formulae III and IV is performed at temperatures of between approximately $-5°$ C. and approximately $30°$ C., for a time substantially between 1 hour and 5 hours. The exact quantities of the reactants brought into contact are not critical, but it is nevertheless preferable to employ at least two molar proportions of the compound of formula IV for each mole of the compound of formula III with the object of obtaining a complete reaction as well as good yields.

The reaction is performed in an organic solvent selected from pyridine, triethylamine, substituted pyridines such as 4-dimethylaminopyridine, picoline, lutidine, and the like; or dimethyl sulphoxide, dichloromethane, 1,2-dichloroethane, dimethylformamide, 1,2-dimethoxyethane, dioxane, tetrahydrofuran, and the like. In the case where the solvent used is not basic, it is necessary to add at least two molar equivalents of an organic base such as pyridine, triethylamine, trimethylamine, and the like.

Alternatively, the reaction between the compounds of formulae III and IV may be performed in the presence of an alkali metal hydride such as sodium hydride, in an organic solvent, for example dioxane, tetrahydrofuran, 1,2-dimethoxyethane, toluene, xylenes, or dipolar aprotic solvents such as dimethyl sulphoxide, dimethylformamide, hexamethylphosphoramide, and the like.

The reaction is performed at the same temperatures and for the same time as are described in the case where an organic base is used.

Furthermore, the new chemical compounds of general formula I, in which $R^1$ has the meaning given above, may be converted to droxicam, of formula II in which $R^2$ represents a 2-pyridyl radical, by heating in an organic solvent such as pyridine, at temperatures of between $25°$ and $60°$ C., for a time between 5 hours and 24 hours.

These compounds of general formula I hence find their application in the preparation of droxicam.

The reaction leading to the compounds of general formula I appears to take place with the initial formation of an organic salt or an alkali metal salt, the anion of which reacts with a chloroformate of formula IV. The subsequent formation of a second anion and further reaction with a compound of formula IV would give rise to the formation of the compounds which are the subject of the present application, of general formula I. It is not, however, the Applicant's intention to be limited by an interpretation of this kind.

The reaction may be represented schematically as follows:

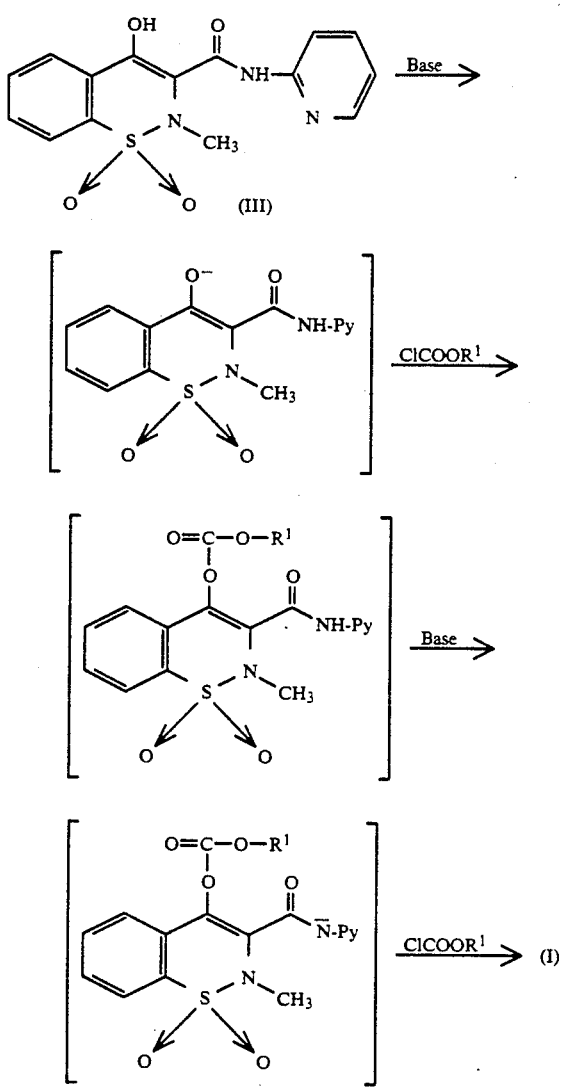

The present invention hence applies also to the use of the compounds of general formula I as synthesis intermediates for medicinal products derived from oxazinobenzothiaze, especially droxicam.

The preparation of derivatives of general formula I and the formation of droxicam, of general formula II ($R^2$=2-pyridyl), from derivatives of general formula I will be described below by way of a simple non-limiting example.

EXAMPLE 1

Preparation of
N-ethoxycarbonyl-N-(2-pyridyl)-4-ethoxy-carbonyloxy-2-methyl-2H-1,2-benzothiazine-3-carboxamide 1,1-dioxide 90 ml (0.945 mole) of ethyl chloroformate are added slowly to a suspension of 75 g (0.226 mole) of N-(2-pyridyl)-4-hydroxy-2-methyl-2H-1,2-benzothiazine-3-carboxamide 1,1-dioxide in 225 ml of anhydrous pyridine at 0° C., and the temperature is maintained below 10° C. The mixture is stirred for 1 hour and the reaction medium is allowed to come to room temperature (approximately 20° C.). The suspension is poured into 1,200 ml of ice-cold water, the mixture is stirred for 1 hour at 0°–5° C. and filtered and the product is washed with 200 ml of cold water.

The crude product is mixed with stirring with 200 ml of cold acetone, the mixture is filtered and the residue is washed with 100 ml of cold acetone. 96.4 g (yield: 90%) of a white product of melting point 144°–146° C. are obtained. On recrystallization with ethyl acetate, a yellowish-white solid of melting point 148°–149° C. is obtained.

Spectroscopic data: $^1$H NMR, δ, [DMSO-$d_6$]: 1.10 (t,3H); 1.30 (t,3H); 3.30 (s,3H); 4.24 (q,2H); 4.35 (q,2H); 7.42 (m,2H); 7.60 (m,1H); 7.80 (m,2H); 7.96 (m,2H); 8.53 (d,1H).

IR(KBr): 1755, 1748, 1690, 1335, 1245, 1015, 715 cm$^{-1}$.

EXAMPLE 2

Preparation of
N-ethoxycarbonyl-N-(2-pyridyl)-4-ethoxy-carbonyloxy-2-methyl-2H-1,2-benzothiazine-3-carboxamide 1,1-dioxide.

2.62 g of sodium hydride in 55% suspension in mineral oil are washed with n-pentane in order to separate the oil after settling has taken place. 100 ml of tetrahydrofuran are added to the resulting sodium hydride (1.44 g, equivalent to 0.06 mole) and, in an ice bath at 5° C., 8.3 g (0.025 mole) of N-(2-pyridyl)-4-hydroxy-2-methyl-2H-1,2-benzothiazine-3-carboxamide 1,1-dioxide are added. The mixture is stirred for one hour while the temperature is maintained at between 0° and 5° C., and 6.7 ml (0.07 mole) of ethyl chloroformate are added. The mixture is stirred for between 1 and 2 hours until it comes to room temperature (20° C.), and it is filtered, the filtrate is evaporated to dryness, the residue is washed with cold water and 11.2 g (yield: 94%) are obtained. On recrystallization with ethyl acetate, a product of melting point 148°–149° C., of spectroscopic characteristics identical to those stated in Example 1, is obtained.

EXAMPLE 3

Under working conditions applied in a manner similar to those described in Examples 1 and 2, the following compounds may be separated using the appropriate chloroformate of general formula IV.

N-phenoxycarbonyl-N-(2-pyridyl)-4-phenoxycarbonyloxy-2-methyl-2H-1,2-benzothiazine-3-carboxamide 1,1-dioxide;

N-benzyloxycarbonyl-N-(2-pyridyl)-4-benzyloxycarbonyloxy-2-methyl-2H-1,2-benzothiazine-3-carboxamide 1,1-dioxide;

N-methoxycarbonyl-N-(2-pyridyl)-4-methoxycarbonyloxy-2-methyl-2H-1,2-benzothiazine-3-carboxamide 1,1-dioxide.

EXAMPLE 4

Preparation of
5-methyl-3-(2-pyridyl)-2H,5H-1,3-oxazino-[5,6-c][1,2]benzothiazine-2,4(3e,uns/H/ )-dione 6,6-dioxide; droxicam.

90 g (0.189 mole) of N-ethoxycarbonyl-N-(2-pyridyl)-4-ethoxycarbonyloxy-2-methyl-2H-1,2-benzothiazine-3-carboxamide 1,1-dioxide are suspended in 150 ml of anhydrous pyridine. The mixture is heated to 35° C. and this temperature is maintained for 15 hours. The mixture is cooled to room temperature (20° C.) and poured into 750 ml of water. The precipitate obtained is filtered off and washed with water and finally with acetone.

64 g (yield: 95%) are thereby obtained. On recrystallization with 1,2-dichloroethane, a crystalline white solid of melting point 261°-263° C. is obtained.

Spectroscopic data: $^1$H NMR, δ, [DMSO-$d_6$]: 3.02 (s,3H); 7.52 (m,2H); 7.92 (m,5H); 8.52 (d,1H).

IR (KBr): 1185, 1355, 1410, 1640, 1710, 1790 cm$^{-1}$.

ANTI-INFLAMMATORY ACTIVITY (Inhibition of carrageenan-induced oedema)

The anti-inflammatory activity of the compound of Example 1 was studied by determining the inhibition of carrageenan-induced oedema in Wistar rats and comparing it with phenylbutazone. The method followed was that described by Winter et al. (Proc. Soc. Exp. Biol. Med. 1982; 111; 544-547). The ED$_{50}$ was calculated from the results obtained 3 hours after oral administration of the products, that is to say also 2 hours after the injection of carrageenan into each foot (0.1 ml of 2% carrageenan solution via the subplantar route).

The summary of the results obtained is as follows:

Inhibition of carrageenan-induced oedema in Wistar rats 3 hours after administration of the product:

| Product | Dose (mg/kg, p.o.) | N | Oedema inhibition % | ED$_{50}$ (mg/kg) |
|---|---|---|---|---|
| Example 1 | 2.5 | 10 | 33.8 | |
| | 5 | 10 | 54.3 | |
| | 10 | 10 | 63.8 | 5.6 |
| | 40 | 10 | 65.5 | |
| Phenyl- | 3.12 | 10 | 21.5 | |
| butazone | 12.5 | 10 | 46.6 | |
| | 25 | 10 | 52.1 | 19.6 |
| | 50 | 10 | 63.5 | |

Three particular pharmaceutical dosage forms of the derivatives which are the subject of the present invention are shown below by way of examples.

| Example of formula per hard gelatin capsule | |
|---|---|
| N-Ethoxycarbonyl-N-(2-pyridyl)-4-ethoxycarbonyloxy-2-methyl-2H-1,2-benzothiazine-3-carboxamide 1,1-dioxide | 0.020 g |
| Lactose | 0.136 g |
| Talc | 0.0016 g |
| Magnesium stearate | 0.0016 g |
| Aerosil 200 | 0.0008 g |
| Capsule weight | 0.160 g |
| Example of formula per tablet | |
| N-Ethoxycarbonyl-N-(2-pyridyl)-4-ethoxycarbonyloxy-2-methyl-2H-1,2-benzothiazine-3-carboxamide 1,1-dioxide | 0.020 g |
| Avicel pH 102 | 0.046 g |
| Lactose | 0.055 g |
| Primogel | 0.003 g |
| Polyvinylpyrrolidone | 0.005 g |
| Magnesium stearate | 0.011 g |
| Tablet weight | 0.100 g |
| Example of formula per suppository | |
| N-Ethoxycarbonyl-N-(2-pyridyl)-4-ethoxycarbonyloxy-2-methyl-2H-1,2-benzothiazine-3-carboxamide 1,1-dioxide | 0.050 g |
| Monolene | 1.950 g |
| Suppository weight | 2.000 g |

We claim:

1. A chemical compound corresponding to the formula I

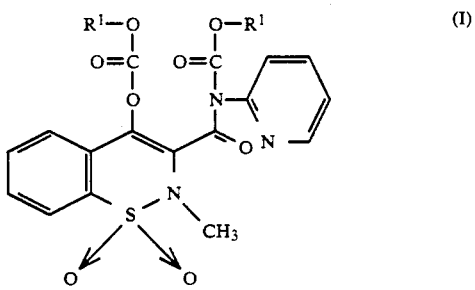

in which:

R$^1$ represents a lower alkyl radical (having one to four carbon atoms), a phenyl radical or a benzyl radical.

2. Compound of formula I according to claim 1, characterized in that it is N-ethoxycarbonyl-N-(2-pyridyl)-4-ethoxycarbonyloxy-2-methyl-2H-1,2-benzothiazine-3-carboxamide 1,1-dioxide.

3. A pharmaceutical composition, characterized in that it contains, apart from a pharmaceutically acceptable vehicle, an anti-inflammatory amount of an active principle comprising a compound according to claim 1 or 2.

4. A method for treating inflammation in a patient which comprises administering to said patient an anti-inflammatory amount of a compound of claim 1 or claim 2.

* * * * *

UNITED STATES PATENT AND TRADEMARK OFFICE
CERTIFICATE OF CORRECTION

PATENT NO. : 5,132,304

DATED : July 21, 1992

INVENTOR(S) : Ribalta-Baro et al.

It is certified that error appears in the above-indentified patent and that said Letters Patent is hereby corrected as shown below:

Column 1, line 62, delete [4058] and insert —408—.

Column 4, line 61, delete (3e,uns/H/)] and insert —(3H)—.

Signed and Sealed this

Twenty-first Day of May, 1996

Attest:

BRUCE LEHMAN

*Attesting Officer*   *Commissioner of Patents and Trademarks*